United States Patent
Haveri

(10) Patent No.: US 8,739,779 B2
(45) Date of Patent: Jun. 3, 2014

(54) BRANCHING UNIT FOR DELIVERING RESPIRATORY GAS OF A SUBJECT

(75) Inventor: Heikki Antti Mikael Haveri, Palakoskentie (FI)

(73) Assignee: General Electric Company, Schenectady, NY (US)

( * ) Notice: Subject to any disclaimer, the term of this patent is extended or adjusted under 35 U.S.C. 154(b) by 851 days.

(21) Appl. No.: 12/545,188

(22) Filed: Aug. 21, 2009

(65) Prior Publication Data
US 2010/0065053 A1 Mar. 18, 2010

(30) Foreign Application Priority Data
Sep. 15, 2008 (EP) .................................... 08396013

(51) Int. Cl.
| A62B 9/04 | (2006.01) |
| A61M 15/00 | (2006.01) |
| A61M 16/10 | (2006.01) |
| A61M 16/00 | (2006.01) |
| A62B 9/06 | (2006.01) |

(52) U.S. Cl.
USPC ............ 128/202.27; 128/203.12; 128/207.14

(58) Field of Classification Search
USPC ............ 128/202.27, 205.24, 207.12, 207.16, 128/912
See application file for complete search history.

(56) References Cited

U.S. PATENT DOCUMENTS

| 4,320,754 A | 3/1982 | Watson et al. |
| 4,852,563 A * | 8/1989 | Gross ........................ 128/202.27 |
| 5,433,195 A | 7/1995 | Kee et al. |
| 5,720,282 A | 2/1998 | Wright et al. |
| 5,735,271 A * | 4/1998 | Lorenzen et al. ........ 128/207.16 |
| 6,029,666 A | 2/2000 | Aloy et al. |
| 6,082,361 A * | 7/2000 | Morejon ................... 128/207.15 |
| 6,530,370 B1 * | 3/2003 | Heinonen ................. 128/200.16 |
| 6,539,937 B1 * | 4/2003 | Haveri ...................... 128/200.21 |
| 6,579,254 B1 * | 6/2003 | McNary et al. ................. 604/27 |
| 6,615,835 B1 * | 9/2003 | Cise et al. ................. 128/207.14 |
| 6,978,779 B2 * | 12/2005 | Haveri ...................... 128/200.16 |
| 2011/0284007 A1 * | 11/2011 | Pierre ........................ 128/207.16 |

FOREIGN PATENT DOCUMENTS

| WO | 8108675 A | 10/1981 |
| WO | 0056385 A1 | 9/2000 |

OTHER PUBLICATIONS

EP Official Action from EP Application No. 08396013.8 dated Mar. 30, 2011.

* cited by examiner

Primary Examiner — Oren Ginsberg
(74) Attorney, Agent, or Firm — Global Patent Operation; Marc A. Vivenzio

(57) ABSTRACT

A branching unit for delivering a respiratory gas of a subject is disclosed herein. The branching unit includes a first limb for delivering an expiratory gas during an expiratory phase and a second limb for delivering an inspiratory gas during an inspiratory phase. The branching unit also includes a third limb connecting with the first limb and the second limb for delivering both said expiratory gas and said inspiratory gas and at least one port for a medical appliance.

16 Claims, 2 Drawing Sheets

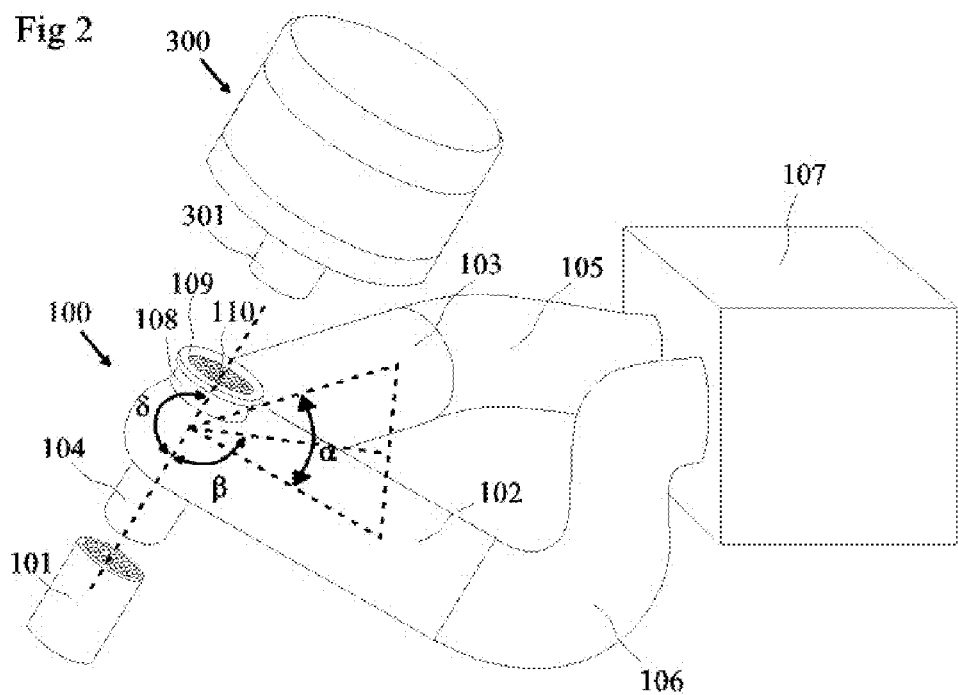
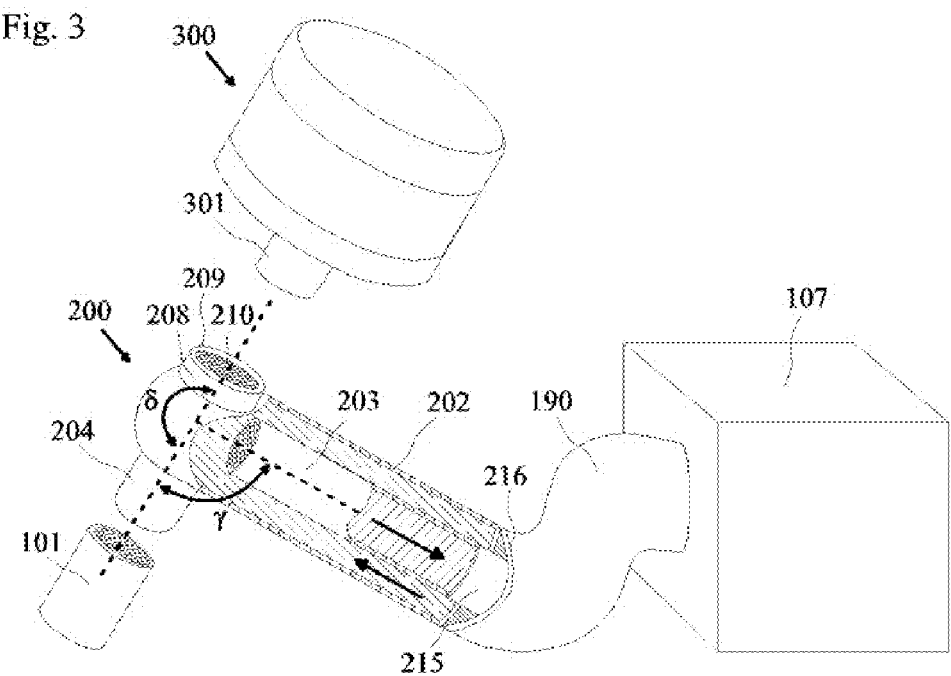

BRANCHING UNIT FOR DELIVERING RESPIRATORY GAS OF A SUBJECT

CROSS-REFERENCE TO RELATED APPLICATIONS

This application claims priority under 35 U.S.C. §119(a)-(d) or (f) to prior-filed, co-pending European Patent Office patent application number 08396013.8, filed on Sep. 15, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

REFERENCE TO A SEQUENCE LISTING, A TABLE, OR COMPUTER PROGRAM LISTING APPENDIX SUBMITTED ON COMPACT DISC

Not Applicable

BACKGROUND OF THE INVENTION

1. Field of the Invention

This disclosure relates to a branching unit for delivering a respiratory gas of a subject.

2. Description of Related Art

Tidal volume (TV) is an amount of an air inspired or taken into the lungs in a single breath. TV is also dependent on the sex, size, height, age and a health etc. of a patient. In general TV also decreases as the size of the patient decreases. In an average healthy adult, TV is about 400-600 ml whereas in an average healthy neonate, that measures 3.5-4 kg and is 50 cm tall, TV is approximately 25-50 ml. On the other hand, in an average premature neonate that measures only 500 grams TV is only about 2-3.5 ml. TV of a smaller patient's is very difficult to measure, but it can be approximated to 4-7 ml/kg, applying a general rule of thumb for approximating the TV of the human lung. In practice the TV of the patient suffering pulmonary system deficiency is normally much less than the approximation gives.

When the patient is mechanically ventilated with a conventional ventilator, an endotracheal tube is placed into a trachea so that it goes through oral or nasal cavity and larynx. The other end of the endotracheal tube is connected to a breathing circuit Y-piece through a luer type connector. If the patient is gas monitored with a mainstream or sidestream gas analyzer, an airway adapter used for sampling the breathing gas that is analyzed by the gas analyzer is normally connected between connectors of the endotracheal tube and the breathing circuit Y-piece. During an inspiration the fresh breathing gas containing higher oxygen ($O_2$) concentration flows into the patients lungs through an inspiratory limb of the breathing circuit Y-piece, the airway adapter, the endotracheal tube and their connectors, then to a trachea, a bronchus, a bronchi, bronchioles and finally reaching an alveoli deep in the lungs, where all the gas exchange actually occurs. Carbon dioxide ($CO_2$) molecules in hemoglobin of a blood flowing in tiny blood vessels around the alveoli are replaced with $O_2$ molecules in the fresh breathing gas through the thin walls of the alveoli. $O_2$ molecules take their place in the hemoglobin, whereas $CO_2$ molecules flow out from the patient within the used expired breathing gas, through the same path as the fresh gas came in during the inspiration. Thus a gas concentration of the breathing gas measured by the gas analyzer is somewhat proportional to the gas concentration in the blood.

A volume in a space between a connection of the inspiratory and expiratory limbs of the Y-piece and the patient's mouth or nose, a beginning of oral and nasal cavities, is called a mechanical dead volume or dead space, whereas the volume in a space between patient's mouth or nose and the entrance of alveoli is called an anatomical dead volume. The part of the lung that is injured or damaged for some reason and does not participate for the gas exchange is called more specific a physical dead volume. It is obvious that as the used breathing gas flows out from the patient's lungs through the expiratory limb during expiration, a part of the used gas newer exits a pulmonary system, as well as the patient side of the breathing circuit, but remains in the mechanical and anatomical dead volume. Then as the fresh gas is inspired in to the lungs through the inspiratory limb the used gas already in the anatomical and mechanical dead volume flows into the lungs before the fresh gas. The used gas fills up some or all of the alveoli depending on a ratio of the dead volume and TV or at least mixes up with the fresh gas decreasing the concentration of $O_2$ as well as increasing the concentration of $CO_2$ in the lungs, which in turn decreases the gas exchange in the alveoli. This means that the larger the dead space, the larger the volume of the used gas, with a low $O_2$ and high $CO_2$ concentration, that flows back to the patients lungs during the inspiration and worse the gas exchange in the alveoli. In other words, if the total dead volume were larger than TV or as large as TV, the patient would not get any fresh gas into the lungs, but respires the used gas back and forth in the dead volume. In practice a diffusion of gases assists the gas exchange over the dead volume little, especially when there is some movement of gases such as high frequency ventilation evolved, but the overall gas exchange in the alveoli would be lethal or dangerously poor anyway.

The anatomical dead volume is almost impossible to reduce, but it is proportional to the size and the physical condition of the patient. The mechanical dead volume depends on a breathing circuit design, defined by the inner diameter of the tubing, connectors and additional accessories. Additional accessories are usually different type of breathing circuit connectors such as a so-called peep saver, T-connector, L-connector etc. used to build up a suitable circuit for the treatment of the patient and to add devices such as gas analyzers, humidifiers, nebulizers etc to the circuit. These additional accessories and devices increase the mechanical dead volume considerably. Obviously the mechanical dead volume is more critical for smaller patients with smaller TV or patients suffering barotraumas etc., which also decrease TV and for this reason many devices cannot be used for the treatment of smaller patients.

The conventional patient side part of the breathing circuit, which is also shown in FIG. 1, usually consists of an endotracheal tube 1, male type luer connector 2, so-called peep saver 3, T-piece 4 used to connect a humidifier, a nebulizer or a similar device (not shown) and Y-piece 5 that connects the patient side part of the breathing circuit to the ventilator through breathing circuit tubing (not shown).

The other end of endotracheal tube 1 enters the patient's trachea (not shown) and the other end contains a male type luer connector 2. The connecter 2 is oftentimes firmly attached to the end of endotracheal tube 1. The conventional, so-called peep saver 3 contains three tubular ports. The first port 31, which is a female type luer connector, can be connected to the male type luer connector 2 at the end of endotracheal tube 1. The second port 32 straight at the opposite side of the first port 31 contains an elastic part 33 with a thin membrane 34 in the middle of it, made of material such as rubber that can be pierced with a catheter. The catheter is used to suck mucus, blood and body fluids from the patient's lungs to keep the lungs open for the gas exchange. The third port 35 is a male type luer connector that is adjacent to and in sharp angle relative to the second port 32. The conventional T-piece 4 also contains three tubular openings. The first port 41 of the T-piece 4, which is a female type luer connector, can be connected to the male type third port 35 of peep saver 3 or the male type luer connector 2 at the end of endotracheal tube 1. A second port 42 of the T-piece 4 is used to connect a humidifier, a nebulizer or a similar device in to the breathing circuit so that the fluid flows through an opening 43 in the port 42 of the T-piece 4 into the breathing gas flowing by the port. The opening 43 can be closed with a cap 44 to prevent the pressure and the flow inside the breathing circuit to escape through the opening when the connectable device is not used. A third port 45 is a male type luer connector. The conventional Y-piece 5 contains three tubular ports as well. A first port 51, which is a female type luer connector, can be connected to the male type luer third port 45 of the T-piece 4, the male type luer third port 35 of the peep saver 3 or the male type luer connector 2 at the end of endotracheal tube 1. An inspiratory limb 52 of the Y-piece 5 connects to a ventilator through an inspiratory tubing to carry inspiratory fresh gas through the circuit into the patient whereas an expiratory limb 53 connects to the ventilator through an expiratory tubing to carry expiratory gas out from the patient. If a breathing gas analyzing is desired the adapter consisting male and female type luer connectors is usually connected between the connector 2 of endotracheal tube 1 and the peep saver 3 or the peep saver 3 and the T-piece 4 or the T-piece 4 and the Y-piece 5 (not shown in FIG. 1).

All of the male and the female type luer connectors in the circuit are standard size and all the males and the females connect to each other regardless of which connectors or pieces are connected together. Although all the pieces and connectors can be placed freely into different locations in the circuit the peep saver 3 should be connected always to the connector 2 of the endotracheal tube 1 to ensure that the catheter has the shortest and free entrance into the patient's lungs. The free placement of different parts thus causes a disadvantage for misplacing the parts.

Conventional humidifiers and nebulizers are big and clumsy thus they are normally connected between the inspiratory lines close to the ventilator. If the nebulizer is desired closer to the patient, to achieve better delivery efficiency, it is connected to the T-piece. Because of the device size the T-piece is also relatively big and its dead volume large, approximately 10-15 ml. Furthermore as the device is connected to the T-piece the large dead volume of the device itself, which may be tens of milliliters, is also added to the total dead volume of the circuit. For this reason the T-connector is usually placed into the circuit for that time only to enable the delivery of fluids into the patient's lungs. The disadvantage is that the circuit is opened twice for each treatment, as the T-piece is connected on and off, and the pressure and the flow inside the circuit escape. Especially the pressure drop inside the circuit is dangerous for the unhealthy lungs since the lungs and the alveoli deep in the lungs used for the gas exchange collapse each time the circuit is opened. During the collapse the gas exchange is decreased considerably and the recovery from the collapse may take even several hours and usually needs expensive and difficult further medication.

Further disadvantage is the opening 43 where the pressure and the flow escape similarly each time it is opened. Another disadvantage, especially with nebulizers, is the location of the second port 42 of the T-piece 4. Most of the nebulizers generate the aerosol so that the speed of the fluid drops is high. As the drops come out from the nebulizer and through the second port 42 they hit into the wall between the first port 41 and the third port 45 at the opposite side of the nebulizer exit. Thus many of the generated fluid drop newer reach the patient's lungs, but turn into a liquid in the circuit again and cause problems for the patient and decrease the delivery efficiency.

The peep saver is continuously used at least with pediatric and adult patients and the lungs are usually sucked empty of body fluids with a catheter through the peep saver many times per day at least in ICU (intensive care unit). Although its advantage of saving the pressure and the flow inside the circuit during the treatment the disadvantage is the large dead volume, approximately 10-15 ml, it adds to the circuit. Similarly the connector 2 of the endotracheal tube 1 as well as the first port 51 of the Y-piece 5 both increase the dead volume of the circuit by approximately 2-3 ml thus the increase together is approximately 4-6 ml.

Thus when using the patient side part of the breathing circuit, as also shown in FIG. 1, the overall size and the weight of the circuit is huge not to mention the very large overall dead volume, approximately 25-35 ml.

Also the number of male and female connections, each causing step like change into the breathing circuit flow path, as well as large volumes of each connector and piece, cause turbulences into the gas flow that in turn mix the fresh gas flowing towards the patient and the used gas flowing out from the patient decreasing the gas exchange in the lungs.

BRIEF SUMMARY OF THE INVENTION

The above-mentioned shortcomings, disadvantages and problems are addressed herein which will be understood by reading and understanding the following specification.

In an embodiment a branching unit for delivering a respiratory gas of a subject includes a first limb for delivering an expiratory gas during an expiratory phase, a second limb for delivering an inspiratory gas during an inspiratory phase and a third limb connecting with the first limb and the second limb for delivering both the expiratory gas and the inspiratory gas. A branching unit for delivering a respiratory gas of a subject also includes at least one port for a medical appliance.

In another embodiment, a branching unit for delivering a respiratory gas of a subject includes a first limb for delivering an expiratory gas during an expiratory phase, a second limb for delivering an inspiratory gas during an inspiratory phase and a third limb connecting with the first limb and the second limb for delivering both the expiratory gas and the inspiratory gas. The branching unit for delivering a respiratory gas also includes at least one port for a possible medical appliance and which port is equipped with a shutter closing the port, but allowing if necessary the medical appliance to be inserted into or through the port.

In yet another embodiment a branching unit for delivering a respiratory gas of a subject includes a first limb for delivering an expiratory gas during an expiratory phase, a second limb for delivering an inspiratory gas during an inspiratory phase, a third limb connecting at an angle of between 30° and 180° degrees with at least one of the first limb and the second limb for delivering both the expiratory gas and the inspiratory gas. A branching unit for delivering a respiratory gas of a subject also includes at least one port for a medical appliance.

Various other features, objects, and advantages of the invention will be made apparent to those skilled in art from the accompanying drawings and detailed description thereof.

BRIEF DESCRIPTION OF THE SEVERAL VIEWS OF THE DRAWINGS

FIG. 2 shows an exploded schematic view of a breathing circuit in accordance with an embodiment; and FIG. 3 shows an exploded schematic view of a breathing circuit in accordance with another embodiment.

DETAILED DESCRIPTION OF THE INVENTION

Figure 1:
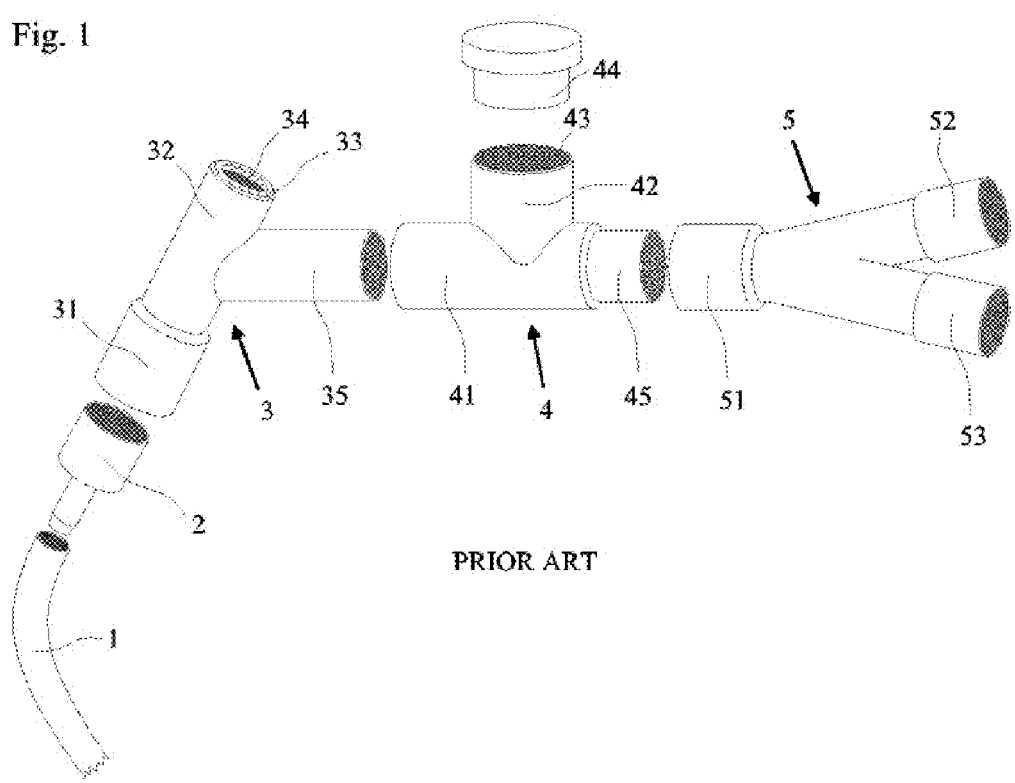
FIG. 1 shows an exploded view of a prior art breathing circuit.

Specific embodiments are explained in the following detailed description making a reference to accompanying drawings. These detailed embodiments can naturally be modified and should not limit the scope of the invention as set fort in the claims.

FIG. 2 shows a patient side part of a breathing circuit according to an embodiment. The new breathing circuit builds up of a branching unit 100 that is connected between an endotracheal tube 101 and a ventilator 107. A medical appliance 300 such as a humidifier, a nebulizer, a catheter or a tube or similar device can be connected straight to the branching unit 100.

The branching unit 100 contains a first limb 102 for delivering an expiratory gas during the expiration phase, a second limb 103 for delivering an inspiratory gas during the inspiration phase and a third limb 104 connecting with the first limb 102 and the second limb 103 for delivering both the expiratory and inspiratory gas. The third limb 104 can be connected to either an airway adapter of a gas analyzer (not shown in FIG. 2) or the endotracheal tube 101. The second limb 103 is equipped with a standard luer type male connector (not shown in the Figures) that fits into standard inspiratory tubing 105 of the breathing circuit. The first limb 102 is also equipped with a standard luer type male connector (not shown in the Figures) that fits into standard expiratory tubing 106 of the breathing circuit. Another end of both the inspiratory tubing 105 and the expiratory tubing 106 is connected to a ventilator 107. A contact angle α between the first limb 102 and the second limb 103 may vary between 0°-180° degrees. Thus the first limb 102 and the second limb 103 may be placed parallel with 0° contact angle α so that there is a small space between the limbs to connect the inspiratory and expiratory tubing to corresponding limbs or the limbs may be placed in series with 180° contact angle α so that they form a continuous straight tube which other end connects to the inspiratory tubing 105 and the other connects to expiratory tubing 106.

Furthermore the branching unit 100 contains at least one port 108, which can be besides an opening on a surface of the branching unit 100 but also a protruding object which can be called as a fourth limb as well. The port 108 may be at an angle of delta (δ) which is 160°-200° degrees with the third limb 104, but preferably it is at an angle of 180° degrees with the third limb 104 in which case it is parallel and straight at the opposite side of the third limb 104 as shown in FIG. 2. The first limb 102, the second limb 103, the third limb 104 and the port 108 form advantageously an integral structure. The port 108 may locate at the branching point of the branching unit, where the first limb 102, the second limb 103 and the third limb 104 separate from each other.

The port 108 comprises a shutter 110 that can allow if necessary the medical appliance 300 to be inserted into or through the port 108 and that can allow if necessary the connection from the medical appliance 300 into the endotracheal tube 101, patients airways and the breathing gas flowing in the breathing circuit. The medical appliance can also be fixed permanently into the port. The shutter 110 may have a form of a membrane which may be surrounded by an elastic part 109, or a similar construction to fix the membrane to the port 108, and which membrane 110 can be thin and made of a material such as rubber or similar that can allow if necessary the medical appliance 300 to be inserted into the port 108 or the shutter 110 may have a form of a slide valve (not shown in figures) that allows opening and closing the passage between the medical appliance 300 and branching unit 100 after connecting the medical appliance into the port 108 or the shutter may be a combination of the slide valve and the membrane. If the shutter is the slide valve it may easily allow the use of existing standard closed system sucking catheters. A practical way is to pierce the membrane with the medical appliance 300.

The catheter as the medical appliance 300 is used to suck mucus, blood and body fluids from the subject's or patient's lungs to keep the lungs open for a gas exchange. The overall area of the thin membrane in the middle of the elastic part 109 is also so large that the very small medical appliance 300 such as the nebulizer e.g. described in U.S. Pat. Nos. 6,530,370 and 6,978,779, containing a small connecting part 301 used to connect the nebulizer into the breathing circuit, can be connected to the port 108 of the branching unit 100 piercing the port 108 through the thin membrane without loosing the peep pressure inside the breathing circuit and the branching unit 100. The thin membrane of the port 108 can be pierced through with other medical appliances 300 such as a fibers scope, or similar device as well, to examine the lungs without loosing the peep pressure inside the breathing circuit and the branching unit 100.

A contact angle β, between the third limb 104 and at least one of the first limb 102 and the second limb 103 may vary between approximately 30°-180° degrees or the plane formed by the first limb 102 and the second limb 103 in regard to the third limb 104 and the port 108 may vary between approximately 30°-180° degrees. Preferably the contact angle β is between 45°-135° degrees. The contact angle may be fixed, but in case adjustable, it may contain turning joint of some form, to ease the positioning of the branching unit 100 relative to the subject.

The branching unit 100 may have other structural forms as well, for example such that it fits into the coaxial breathing circuit tubing 190 as shown in FIG. 3. The coaxial breathing circuit tubing 190 comprises an inspiratory tubing 215 as an inner tube for the inspiratory gas to flow towards the subject, which is placed middle inside the outer tube, which is an expiratory tubing 216 so that the expiratory gas can flow in the space between the inner and outer tube out from the subject towards the ventilator 107. The benefit in transferring gases within nested tubing is that the warm expiratory gas coming out from the subject and flowing between the inspiratory tubing 215 and the expiratory tubing 216 warms up the cooler, fresh inspiratory gas flowing inside the inspiratory tubing 215 towards the subject. When the fresh gas is pre-heated by the ventilator 107, or other device, the temperature of inspiratory gas flowing inside the inspiratory tubing 215 may remain fairly constant when entering towards the subject. It is important to maintain a steady body temperature of the subject, because the cool inspiratory gas may lower the body temperature of the patient.

The branching unit 200 in FIG. 3 comprises a first limb 202 for delivering an expiratory gas during the expiration phase, a second limb 203 for delivering an inspiratory gas during the inspiration phase and a third limb 204 for delivering both the expiratory and inspiratory gas. The third limb 204 can be connected to either an airway adapter of a gas analyzer (not shown in FIG. 3) or the endotracheal tube 101. The second limb 203 is equipped with a standard luer type male connector (not shown in the Figures) that fits into standard coaxial inspiratory tubing 215 of the breathing circuit. The first limb 202 is also equipped with a standard luer type male connector (not shown in the Figures) that fits into the standard expiratory tubing 216 of the breathing circuit. Another end of both the inspiratory tubing 215 and the expiratory tubing 216 is connected to the ventilator 107.

Furthermore the branching unit 200 of FIG. 3 contains a port 208 similar to the one shown in FIG. 2 and explained above. The port 208 may locate at the branching point of the branching unit, where the first limb 202, the second limb 203 and the third limb 204 separate from each other. The port 208 comprises a shutter 210 that can allow if necessary the medical appliance 300 to be inserted into the port 208 and that can allow if necessary the connection from the medical appliance 300 into the endotracheal tube 101, patients airways and the breathing gas flowing in the breathing circuit. The shutter 210 may have a form of a membrane which may be surrounded by an elastic part 209, or a similar construction to fix the membrane to the port 1 208, and which membrane can be thin and made of a material such as rubber or similar that can allow if necessary the medical appliance 300 to be inserted into the port 208 or the shutter 210 may have a form of a slide valve (not shown in figures) that allows opening and closing the passage between the medical appliance 300 and branching unit 200 after connecting the medical appliance into the port 208 or the shutter 210 may be a combination of the slide valve and the membrane. If the shutter 210 is the slide valve it may easily allow the use of existing standard closed system sucking catheters. The contact angle γ between the first limb 202 and the second limb 203 inside the first limb 202 as well as the third limb 204 and the port 208, dashed lines representing the center axis of the limbs, may vary between approximately 30°-180° degrees. The contact angle may be fixed, but in case adjustable it may contain a turning joint of some form, to ease the positioning of the breathing circuit relative to the patient. Otherwise the use and other features of FIG. 3 branching unit 200 can be identical with the branching unit 100 of FIG. 2.

Branching unit 100, 200 may also contain more than one port 108, 208. The first of the ports 108, 208 may be located straight on the opposite side of port 104, 204 and the second port for example besides and between the ports 108, 208 and 104, 204. The second port could be used for example for longer period of time, continuous drug delivery or similar and the first port could be used for a catheter to suck mucus and body fluids from the trachea and lungs. The disadvantage in increasing the number of ports to the branching unit 100, 200 is it may increase the branching unit complexity, the usage of it and the expense of the branching unit.

The advantage of this new multifunctional branching unit 100, 200 is it combines the functionality of so-called peep saver 3 shown in FIG. 1 and connectivity for the medical device such as the nebulizer or similar device through one port or limb. In practice at least three different parts and functions are combined to one branching unit 100, 200, which then represents the whole patient side breathing circuit together with the endotracheal tube 101 connected to it. Also the size and the weight of the total system, which is located in front of the patients face at the end of the endotracheal tube, is reduced considerably. Smaller size leaves more space for the hospital personnel to operate especially during surgeries around the head area in OR. The lighter weight reduces the risk of endotracheal tube flow path to collapse and together with the smaller size the risk that the moving patient disengages the system unintentionally is decreased. The branching unit 100, 200 may also keep the pressure and the flow inside the breathing circuit and the branching unit 100,200 in all situations although the medical appliances 300 are removed or connected. Furthermore the branching unit 100, 200 preferably does not contain any additional corners and connections that cause mixing of gases, which decrease the efficiency of gas exchange and decrease the breathing gas concentration measurement measured with the gas analyzer. Also the overall dead volume of the breathing circuit and the branching unit 100, 200 is minimized to less than 1 ml even for the largest size of subjects by reducing conventional parts and connectors as well as combining functions to the port 108, 208, which is located outside the volume, where the inspiratory and expiratory gases intermix causing re-breathing of gases, other words the dead volume. Actually the new design and minimal overall dead volume enables the continuous use of the medical appliances 300 that had to be removed from the prior art system because of the dead volume they added and flow disturbances they generated. Furthermore the port 108, 208 is positioned in line with the third limb 104, 204 so that as the medical appliance 300 such as the nebulizer, or similar device, is connected to the port, the liquid spray it injects during inspiration, flows straight through the endotracheal tube 101 in to the subject's lungs and does not hit the corners and the wall of the breathing circuit or the branching unit 100, 200 as in conventional systems. In addition the overall breathing circuit and the branching unit 100, 200 becomes extremely small in size and weight compared to the conventional systems. Also the overall cost becomes much less expensive since there is only one simple piece instead of many.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A branching unit for delivering a respiratory gas comprising:
   a first limb connectable to an expiratory gas tube for delivering an expiratory gas during an expiratory phase;
   a second limb connectable to an inspiratory gas tube for delivering an inspiratory gas during an inspiratory phase;
   a third limb connected with said first limb and said second limb and connectable to an endotracheal tube for delivering both said expiratory gas and said inspiratory gas;
   at least one port for a medical appliance, said at least one port equipped with a shutter configured to close said at least one port but to allow if necessary said medical appliance to be inserted into or through said at least one port, said shutter being a membrane that is pierceable to enable insertion of said medical appliance into or through said at least one port without requiring removal of the shutter from said at least one port; and
   wherein each of said first limb, said second limb, said third limb, and at least one port of said at least one port defines an internal lumen and a corresponding longitudinal axis extending through said internal lumen, and all of said longitudinal axes intersect at a common point internal to said branching unit.

2. The branching unit according to claim 1, wherein said first limb, said second limb, said third limb and said at least one port are configured to form an integral structure.

3. The branching unit according to claim 1, wherein said third limb is at an angle of between 30° and 180° degrees with at least one of said first limb and said second limb.

4. The branching unit according to claim 1, wherein said at least one port is at an angle of 160°-200° degrees with said third limb.

5. The branching unit according to claim 1, wherein said first limb is at an angle of 0°-180° degrees with said second limb.

6. The branching unit according to claim 1, wherein said second limb is inside said first limb.

7. The branching unit according to claim 1, wherein said medical appliance is one of a humidifier, a nebulizer, a catheter, a fiber scope and a tube.

8. The branching unit according to claim 1, wherein said longitudinal axes are central longitudinal axes.

9. The branching unit according to claim 1, wherein said common point is located at a common junction of said first limb, said second limb and said third limb.

10. The branch unit according to claim 1, wherein the shutter is locates at a branching point of the branching unit, where said first limb, said second limb and said third limb separate from each other.

11. A branching unit for delivering a respiratory gas comprising:
   a first limb connectable to an expiratory gas tube for delivering an expiratory gas during an expiratory phase;
   a second limb connectable to an inspiratory gas tube for delivering an inspiratory gas during an inspiratory phase;
   a third limb connected with said first limb and said second limb and connectable to an endotracheal tube for delivering both said expiratory gas and said inspiratory gas;
   at least one port for a medical appliance, said at least one port equipped with a shutter configured to close said at least one port but to allow if necessary said medical appliance to be inserted into or through said at least one port, said shutter being a membrane that is pierceable to enable insertion of said medical appliance into or through said at least one port without requiring removal of the shutter from said at least one port; and
   wherein each of said first limb, said second limb, said third limb, and at least one port of said at least one port defines an internal lumen and a corresponding longitudinal axis extending through said internal lumen, and all of said longitudinal axes intersect at a common point internal to said branching unit.

12. The branching unit according to claim 11, wherein said third limb is at an angle of 30°-180° degrees with at least one of said first limb and said second limb.

13. The branching unit according to claim 11, wherein said at least one port is at an angle of 160°-200° degrees with said third limb.

14. A branching unit for delivering a respiratory gas comprising:
   a first limb connectable to an expiratory gas tube for delivering an expiratory gas during an expiratory phase;
   a second limb connectable to an inspiratory gas tube for delivering an inspiratory gas during an inspiratory phase;
   a third limb connecting at an angle of between 30° and 180° degrees with at least one of said first limb and said second limb and connectable to an endotracheal tube for delivering both said expiratory gas and said inspiratory gas;
   at least one port for a medical appliance, said at least one port equipped with a shutter configured to close said at least one port but to allow if necessary said medical appliance to be inserted into or through said at least one port, said shutter being a membrane that is pierceable to enable insertion of said medical appliance into or through said at least one port without requiring removal of the shutter from said at least one port; and
   wherein each of said first limb, said second limb, said third limb, and at least one port of said at least one port defines an internal lumen and a corresponding longitudinal axis extending through said internal lumen, and all of said longitudinal axes intersect at a common point internal to said branching unit.

15. The branching unit according to claim 14, wherein said at least one port is at an angle of 160°-200° degrees with said third limb.

16. The branching unit according to claim 14, wherein the angle between said third limb and at least one of said first limb and said second limb is configured to be adjustable.

* * * * *